United States Patent [19]

Mathews et al.

[11] Patent Number: 4,793,992

[45] Date of Patent: Dec. 27, 1988

[54] HAIR TREATMENT COMPOSITION

[75] Inventors: Roger A. Mathews, Newbury Park; Edward R. Moore, Canoga Park; David W. Cannell, Los Angeles, all of Calif.

[73] Assignee: Redken Laboratories, Inc., Canogo Park, Calif.

[21] Appl. No.: 30,742

[22] Filed: Mar. 25, 1987

[51] Int. Cl.$^4$ .............................................. A61K 7/075
[52] U.S. Cl. ...................................... 424/70; 514/578; 514/665
[58] Field of Search ................... 424/70; 514/21, 561, 514/578, 665; 260/513 N

[56] References Cited

U.S. PATENT DOCUMENTS

| | | | |
|---|---|---|---|
| 3,962,418 | 6/1976 | Birkofer | 424/70 |
| 4,076,800 | 2/1978 | Marsh et al. | 424/70 |
| 4,115,548 | 9/1978 | Marsh et al. | 424/70 |
| 4,132,679 | 1/1979 | Tsutsumi et al. | 252/545 |
| 4,186,188 | 1/1980 | Gumprecht et al. | 424/70 |
| 4,195,077 | 3/1980 | Marsh et al. | 424/70 |
| 4,292,212 | 9/1981 | Melby | 252/547 |
| 4,329,334 | 5/1982 | Su et al. | 424/70 |
| 4,375,421 | 3/1983 | Rubin et al. | 424/70 X |
| 4,393,886 | 7/1983 | Strasilla et al. | 132/7 |
| 4,402,977 | 9/1983 | Grollier et al. | 424/70 |
| 4,419,344 | 12/1983 | Strasilla et al. | 424/70 |
| 4,423,032 | 12/1983 | Abe et al. | 424/70 |
| 4,436,722 | 3/1984 | Matsunaga et al. | 424/70 |
| 4,440,744 | 4/1984 | Strasilla et al. | 424/70 |
| 4,451,385 | 5/1984 | Tavss et al. | 252/132 |
| 4,460,566 | 7/1984 | Abe et al. | 424/70 |
| 4,460,570 | 7/1984 | Strasilla et al. | 424/70 |
| 4,463,017 | 7/1984 | Hidalgo et al. | 514/21 |
| 4,507,280 | 3/1985 | Pohl et al. | 424/70 |
| 4,529,588 | 7/1985 | Smith et al. | 424/70 |
| 4,534,964 | 8/1985 | Herstein et al. | 424/70 |
| 4,564,520 | 1/1986 | Ehrl et al. | 424/70 |
| 4,591,498 | 5/1986 | Kawase et al. | 424/70 |
| 4,592,907 | 6/1986 | Akimoto et al. | 424/70 |

Primary Examiner—George F. Lesmes
Assistant Examiner—Susan S. Rucker
Attorney, Agent, or Firm—Christie, Parker & Hale

[57] ABSTRACT

Hair and skin treating compositions containing hydrolyzed proteins having an average molecular weight in the range of from 500 to 2,000 are enhanced with an approximately equimolar quantity of amino acid derived zwitterion having a molecular weight less than 200, such as taurine. Preferably the taurine is present in such a composition in the range of from 1 to 5% by weight, and the composition has a pH in the range of from 3 to 10, the most preferably from 3 to 7.

19 Claims, No Drawings

HAIR TREATMENT COMPOSITION

BACKGROUND OF THE INVENTION

For many years the cosmetics industry has used products containing hydrolyzed proteins for conditioning of hair and skin. Various reasons exist for the use of degraded proteins in hair and skin care products, not the least of which is their apparent affinity for keratinous tissues. This affinity, called substantivity, is defined as the level of residual binding to the tissues after withdrawal of the product through rinsing. The residual protein associated with the tissue produces a variety of cosmetically desirable effects. For example, hair has improved texture, sheen, and resilience when conditioned with hydrolyzed proteins which bind to the hair.

Generally speaking, hydrolyzed proteins of average molecular weight in the range of from 500 to 2,000 exhibit the greatest substantivity to keratinous tissue. Lower molecular weight protein fragments or their amino acid components penetrate and absorb readily, but are more easily removed by washing or rinsing. High molecular weight or whole proteins may form films on the surface of the tissue, but size prevents absorption and makes the film susceptible to removal by washing or rinsing.

Parameters which are known to affect the substantivity of a given protein hydrolyzate include molecular weight, charge density, concentration in the solution applied to the hair, time of contact and pH. Further the condition of the tissue being treated is an important factor. The more porous the tissue, the greater is the expected degree of substantivity.

In comparing proteins of similar molecular weight, concentration and time of contact, the nature of the protein itself is of prime consideration. Proteins are polyamide polymers of amino acids and the individual amino acid moieties have acidic and basic side chains containing cationic, anionic or neutral groups. The acidic side chains have negative charge and the basic side chains have positive charge in the pH range of most hair and skin care products (pH 3 to pH 10).

Since the keratinous tissue itself is protein, its surface charge varies with pH. Generally, above pH 3.5 the surface of hair and skin has a net negative charge. There is increased ionization of carboxylate groups with subsequent deprotonation of ammonium groups. Since acidic side chains are in excess of basic side chains in keratin, the surface becomes increasingly negative with increasing pH.

The net charge of the protein used in hair treatment compositions is determined by its amino acid composition, i.e., the proportion of acidic and basic side chains. Minimizing the acidic residues or increasing the basicity of the protein results in increased substantivity, since the positive charges of the protein in the treatment solution are attracted to the negative charges of the keratinous surface by ionic interaction.

The ionic charge is of prime importance in increasing substantivity since the ionic "salt" bond is of greater strength than other surface attractions such as hydrogen bonds, van der Waal's forces, or the like. The strength of the ionic bond resists rinsing or washing, leading to improved substantivity.

In general, substantivity to keratinous tissue can be improved by selecting the optimum molecular size for the proteins used in the treatment solution, increasing protein concentration or time of contact, or using proteins of increased basicity, i.e., with positively charged side chains. For example, treatment proteins have been chemically modified through the introduction of quaternary ammonium groups, such as trimethyl ammonium or benzyl dimethyl ammonium groups, to the side chains. The stronger basicity of these groups results in increased attraction for the negatively charged keratinous surface.

Each of these approaches to increasing substantivity has limitations. Lower than optimum molecular size proteins may be more desirable in a given formula for their hygroscopic properties as a hair moisturizer. Higher than optimum molecular size proteins may be more desirable for their film forming, protective, or firming effects on the surface of hair and skin tissue. Such composition variations reduce substantivity.

Increasing the concentration of the protein increases product costs, as well as leading to formulation problems in terms of bacterial contamination, odor and tackiness of the product. The protein hydrolyzates suitable for use are limited to those which have no systemic biological activity. A variety of acidic, basic or enzymatic hydrolyzed natural proteins are commercially available for formulating hair and skin care products. For example, collagen or other animal proteins may be used as starting materials. Hydrolyzed amino acids may be derived from maize, gluten, silk or other proteins.

Increasing contact time between the protein in the treatment solution is undesirable for ease of use by the consumer. Contact time is generally limited to less than 30 minutes, particularly for hair care products.

It is desirable to increase the substantivity of commonly available cosmetic proteins so that they may be used at lower concentrations and may be of other than optimum size for maximum substantivity in order to achieve other desirable properties. Furthermore, it is desirable to have substantivity increase in short contact time. It is important that anything added to such compositions be safe and readily formulated into cosmetic products.

BRIEF SUMMARY OF THE INVENTION

There is, therefore, provided in practice of this invention, according to a presently preferred embodiment a composition for treatment of keratinous tissue comprising an amino acid derived zwitterion having a molecular weight less than 200 in the range of from 0.5 to 10% by weight and a hydrolyzed protein having average molecular weight in the range of from 500 to 2,000 in a proportion approximately equimolar with the zwitterion and having a pH in the range of from 3 to 10.

In a particularly preferred composition the zwitterion is taurine in the range of from 1 to 5% by weight and pH is in the range of 3 to 7. Such a composition can be used with minimal other ingredients as a light hair conditioner which can be applied and left in the hair without rinsing.

DESCRIPTION

The substantivity of a given hydrolyzed protein fraction to keratinous tissue is enhanced by forming a low molecular weight "charge bridge" between the keratin proteins and the protein ingredients in a hair or skin conditioning composition. These charge bridges are formed by strongly dipolar zwitterions. Zwitterions are neutrally charged molecules having both positive and negative charges and a strong dipole moment. Zwitterions having a molecular weight of less than about 200 can, by virtue of small molecular size and unique charge properties, integrate into the protein milieu of keratinous tissue and form active charge binding sites for attraction of charged protein fragments in the conditioning solution. Enhanced binding of the hydrolyzed proteins to the keratinous tissue is provided by this means.

A particularly preferred zwitterion is taurine or 2-amino ethane sulfonic acid. The structure of taurine in acid solution is:

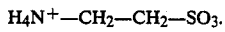

Thus, taurine with a molecular weight of about 125 is a small molecule containing a very strongly positively charged amino group adjacent to a strongly negatively charged sulfonic acid group. The very strong dipole moment of this small zwitterion, its lack of toxicity, and its water solubility make it ideally suited to form charge bridges between the surface of hair and charged protein fragments in a hair conditioning composition.

It is preferred that the zwitterions be amino acid derived and have a molecular weight of less than 200. Such small zwitterions can form small charge bridges and substantially enhance substantivity of the proteins used in cosmetic compositions without significantly changing the desirable attributes of the proteins. Other exemplary zwitterions are derived from beta-alanine, N-trimethyl alanine, N-methyl glycine (sarcosine), N,N-dimethyl glycine, N,N,N-trimethyl glycine, and acetylated betaine, preferably acetylated with small fatty acids.

The proportion of zwitterion in the composition is preferably in the range of from 0.5 to 10% by weight. If the proportion is less than about 0.5%, the enhanced effects due to the zwitterion may be largely masked by the effect of other ingredients in the composition. Effective enhancement of the benefits of the protein binding become significant in about this proportion, depending upon the zwitterion employed.

It is particularly preferred to employ at least 1% taurine in the composition for significant enhancement of protein binding to hair to improve its luster and texture. It becomes prohibitively expensive to employ more than about 10% by weight zwitterion. In addition, a proportionate amount of protein in such a composition may make it tacky. Too much salt formation may occur at hair surfaces and there can be flaking. It is particularly preferred to employ taurine up to 5% by weight in such a composition. There is no apparent salting and no other undesirable effects have been observed.

It is preferred that the proportion of protein in the composition be approximately equimolar with the taurine. Thus, each charged molecule of protein is combined with a single zwitterion and there is no substantial excess of either ingredient. There does not appear to be any substantial detriment of having an excess of either zwitterion or protein in the composition, but conversely there is little apparent benefit from an excess of either.

Generally speaking, it is preferred that the proportion of protein to zwitterion be in the range of from 2:1 to 1:2. It may be desirable, for example, in some compositions to employ this much excess of protein for effects in addition to the ionic bonding to the hair protein, such as film forming. Any greater excess of zwitterion than this proportion is extraordinarily expensive without noticeable benefit.

It is preferred that the hydrolyzed proteins have an average molecular weight in the range of from 500 to 2,000 and preferably from 1,000 to 2,000. Since the hydrolyzed proteins are fragments in various sequences and proportions of amino acids, there are random distributions of molecular weight and charge distribution in the molecules making up the composition. For example, a protein hydrolyzate having an average molecular weight of 2,000 may have a molecular weight distribution from 1,000 to 3,000 in a generally bell-shaped distribution centered at 2,000. Depending upon the origin of the protein, there may be from 10 to 20 amino acid units in such a protein hydrolyzate.

A broad variety of commercially available cosmetic grade hydrolyzed protein derivatives are suitable for practice of this invention. These may encompass unconjugated and conjugated proteins such as metalloproteins, nucleoproteins, phosphoproteins, glycoproteins and lipoproteins. Such proteins are obtainable from many sources including animals, plants, dairy byproducts, molds, fungi, yeasts and bacteria. Typical of the proteins useful for producing charged peptides include casein, collagen, feather keratin, soy protein, maize gluten protein, silk, etc.

Such compositions are preferably water based, containing of from about 50 to 85% water. Ethyl or isopropyl alcohol may also be included in such a composition in the range of from 5 to 30% by weight. Such non-toxic lower alcohols may serve as a solvent for other ingredients in the composition, such as fragrances, and also promote drying in a conditioner left in the hair instead of being rinsed out.

The pH of the hair conditioning composition is preferably in the range of from 3 to 7, and most preferably from 4.5 to 5.5. Such a pH approximates the condition of keratinous tissue for optimum results in a hair treating composition. Citric acid is particularly preferred for adjusting the pH of the composition. Other weak acids such as phosphoric acid may also be used if desired.

A broad variety of other ingredients may be included in such a composition. Surfactants are commonly used for enhanced wetting of the tissue, smoothing of hair and improving its texture. Up to 20% surfactant may be used in compositions that also serve to cleanse the tissues. Various salts, particularly divalent metal salts, may be used in hair conditioning compositions. For example, divalent magnesium in such a composition may serve to bridge adjacent negative charges in amino acids, drawing them together and making the hair stronger and tighter. A variety of oils, emulsifiers, fatty acids, amines, triglycerides, silicones, buffers and the like may also be used in a conventional manner. Such materials affect both the properties of the conditioning composition and the effect on the tissue being treated.

It is particularly preferred to employ taurine in the range of from 1 to 5% by weight and an approximately equimolar proportion of hydrolyzed proteins having an average molecular weight in the range of from 500 to 2,000 in a composition having from 80 to 90% water plus alcohol. Such a composition is quite useful as a "leave in" light or intermediate hair conditioner. Such a hair conditioner can be applied to the hair and left in without rinsing, when free of large amounts of surfactants, oils, emulsifiers and the like.

An exemplary composition has 1% by weight taurine, 6% by weight hydrolyzed protein having an average molecular weight of from 1,500 to 2,000 from 2 to 2-½% magnesium sulfate, and small amounts of perfume and surfactant in a solution that is about 90% water and ethyl alcohol.

A specific example of such a composition forming a light hair texturizer has 59.1% by weight deionized water and 30% ethyl alcohol (SDA-40). One percent taurine is dissolved in this water and alcohol solvent. A mixture of commercially available hydrolyzed proteins is incorporated in the composition. These include 2.0% Crotein SPC (hydrolyzed animal protein) from Croda Chemical Co., 2.0% Crosilk Liquid (a mixture of amino acids derived from hydrolyzed silk protein) from Croda Chemical Co., 2.0% Amino Gluten MG (amino acids derived from maize gluten protein) from Croda Chemical Co, and 0.1% of hydrolyzed protein as described in U.S. Pat. No. 4,186,188 by Gumprecht. The composition also includes 2.5% magnesium sulfate, 1.0% citric acid, 0.25% Tween 20 (a mixture of laureate esters of sorbitol and sorbitol anhydrides condensed with approximately 20 moles of ethylene oxide) from Atlas Powder Company, Wilmington, Del., 1.0% citric acid and 0.05% perfume. Such a composition has a pH of about 5.

Laboratory tests have shown that taurine improves the substantivity of a simple protein-containing hair conditioner. A tritium tagged protein of the type described in the aforementioned Gumprecht U.S. Pat. No. 4,186,188 was used. The presence of taurine approximately equimolar with the protein resulted in a 260% increase in protein binding to hair. The bound protein was retained 350% more efficiently during rinsing. The hair so treated was soft and lustrous.

Taurine may also be useful in reforming or reducing lotions employed in permanent waving of hair, for example. Such wave lotions (as well as various bleaches, tints, and the like) are generally more alkaline than conditioners and often have a pH of from 8 to 10. Hair absorbs alkaline materials and may look "dried out" as a result. The alkali causes hair to swell and the cuticle to stand erect making the hair rough and dull looking. For this reason, such treatments may often be followed by an acidic conditioner to retard the effect of the alkaline treatment materials.

The introduction of taurine in a permanent wave lotion, for example, improves the appearance of the hair without changing the resilience or "crispiness" valued by hairdressers. The hair treated with such a composition does not look as dried out as usual alkaline processed hair and it retains good resilience. These effects, much like other effects in cosmetology, are subjective impressions of hairdressers rather than quantifiable. The reasons for these improvements when taurine is included in the composition have not been determined as yet.

Preferably, in such a composition, taurine is present in the range of from 1 to 5% by weight. There does not appear to be any significant effect below about 1% by weight. No improved results have been observed with concentrations over about 5% by weight. Concentrations at the low end of this range appear sufficient.

An exemplary permanent wave reforming lotion comprises 70.8% by weight deionized water to which is added 13.33% by weight of 60% of ammonium thioglycolate solution. The solution contains 5.0% urea, 4.58% of 28% aqua ammonia and 4.0% of Brij 35 (polyethyleneglycolether of lauryl alcohol) from ICI Americas, Inc., Wilmington, Del. A small amount, 0.5% by weight of hydrolyzed animal protein (Peptein 2,000 from Hormel & Co., Austin, Minn.) and 0.5% trisodium hydroxy ethylene diamine triacetic acid (Perma Kleer 120 from Dow Chemical Co., Midland, Mich.) and fragrance are also included. This composition also includes 1.0% taurine. Hair treated with this lotion does not look as dried out as usual alkaline processed hair and it retains good resilience.

Various embodiments of compositions for treatment or conditioning of keratinous tissue such as hair or skin have been described herein. Many modifications and variations of these will be apparent to one skilled in the art. The use of zwitterions and hydrolyzed proteins may be adapted for use in a variety of pastes, creams, gels, lotions, soaps, shampoos, conditioners, rinses and the like. Various ingredients well known in the art may be employed in such compositions for obtaining the desired properties. It is therefore, to be understood that within the scope of the appended claims, this invention may be practiced otherwise than as specifically described.

What is claimed is:

1. A keratinous tissue treatment composition comprising:
    amino acid derived zwitterion having a molecular weight less than 200 in the range of from 0.5 to 10% by weight; and
    hydrolyzed protein having an average molecular weight in the range of from 500 to 2,000 in a proportion approximately equimolar with the zwitterion; and
    having a pH in the range of from 3 to 10.

2. A composition as recited in claim 1 wherein the zwitterion is present in the range of from 1 to 5% by weight.

3. A composition as recited in claim 2 wherein the zwitterion comprises taurine.

4. A composition as recited in claim 2 wherein the protein has an average molecular weight in the range of from 1,000 to 2,000.

5. A composition as recited in claim 2 comprising water and non-toxic lower alcohol, the water plus alcohol being present the range of from 80 to 90% by weight.

6. A composition as recited in claim 5 comprising 60% water and 30% ethyl alcohol.

7. A composition as recited in claim 2 wherein the pH is in the range of from 3 to 7.

8. A composition as recited in claim 2 wherein the pH is in the range of from 4.5 to 5.5.

9. A composition as recited in claim 1 wherein the zwitterion comprises taurine.

10. A composition as recited in claim 1 wherein the zwitterion comprises an amino positive charge site and a sulfonic negative charge site.

11. A hair treatment composition comprising:
    taurine in the range of from 1 to 5% by weight;
    hydrolyzed protein having an average molecular weight in the range of from 500 to 2,000 in a proportion in the range of from 2:1 to 1:2 relative to the taurine; and
    sufficient water to form a liquid composition having a pH in the range of from 3 to 10.

12. A composition as recited in claim 11 wherein the pH is in the range of from 3 to 7.

13. A composition as recited in claim 11 wherein the pH is in the range of from 4.5 to 5.5.

14. A composition as recited in claim 11 further comprising non-toxic lower alcohol, the total of water plus alcohol being in the range of from 80 to 90% by weight.

15. A composition as recited in claim 11 wherein the protein has an average molecular weight in the range of from 1,000 to 2,000.

16. A method for treating hair comprising contacting the hair with an aqueous solution containing taurine in the range of from 1 to 5% by weight, and hydrolyzed protein having an average molecular weight in the range of from 500 to 2,000 in a proportion approximately equimolar with the taurine.

17. A method as recited in claim 16 wherein the solution has an alkaline pH.

18. A method as recited in claim 16 wherein the solution has a pH in the range of from 3 to 7.

19. A method as recited in claim 16 wherein the solution comprises non-toxic lower alcohol, the total of water and alcohol being in the range of from 80 to 90% by weight.

* * * * *